United States Patent [19]

Gray et al.

[11] 4,122,121
[45] Oct. 24, 1978

[54] CYCLOHEXANE DERIVATIVES

[75] Inventors: Robin Th. Gray; Aaldert J. De Jong, both of Amsterdam, Netherlands

[73] Assignee: Shell Oil Company, Houston, Tex.

[21] Appl. No.: 818,262

[22] Filed: Jul. 22, 1977

[30] Foreign Application Priority Data

Aug. 9, 1976 [GB] United Kingdom ............... 33050/76

[51] Int. Cl.$^2$ .............................................. C07C 47/32
[52] U.S. Cl. ................................ 260/598; 260/348.57; 252/522
[58] Field of Search ......................................... 260/598

[56] References Cited

U.S. PATENT DOCUMENTS

| 2,584,539 | 2/1952 | Bordenca et al. ................... 260/598 |
| 2,710,825 | 6/1955 | Lazier et al. ..................... 260/598 X |
| 2,945,068 | 7/1960 | Booth ............................. 260/598 X |

Primary Examiner—Bernard Helfin

[57] ABSTRACT

Novel cyclohexane derivatives of the formula:

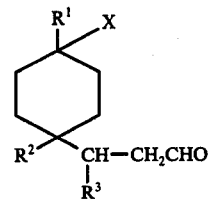

wherein $R^1$ represents an alkyl group, $R^2$ and $R^3$ each represents a hydrogen atom or an alkyl group, and X represents an epoxy or hydroxy group; are useful as aroma chemicals.

5 Claims, No Drawings

CYCLOHEXANE DERIVATIVES

BACKGROUND OF THE INVENTION

This invention relates to novel class of cyclohexane derivatives substituted with carboxaldehyde and hydroxy or epoxy functional groups which are of interest as aroma chemicals.

A variety of hydroxy- and carbonyl-substituted organic compounds are known in the art to possess aroma properties which are useful in the perfumery field. These compounds, which can be of natural or synthetic origin, include hydroxy-aldehydes, esters, aldehydes, ketones and alcohols, having a broad spectrum of perfume-like odors. While, as noted, the aromas from known compounds or combinations of compounds can be quite varied, there still exists a continuing need for new compounds which accent particular fragrances or other odorant properties, especially when such compounds can be obtained from both natural and synthetic sources.

SUMMARY OF THE INVENTION

A novel class of cyclohexane derivatives ring substituted with aliphatic carboxaldehyde groups and hydroxy or epoxy moieties have now been found which possess distinctive floral odors. This novel class of cyclohexane derivatives is represented by the general formula (I):

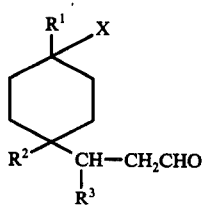

(I)

wherein $R^1$ represents an alkyl group; $R^2$ and $R^3$ each represents a hydrogen atom or an alkyl group; and X represents an epoxy or hydroxy group.

DESCRIPTION OF THE PREFERRED EMBODIMENTS

Preferred cyclohexane derivatives of formula (I) above are those in which $R^1$ is an alkyl group of 1 to 4 carbon atoms and $R^2$ and $R^3$ represent hydrogen or an alkyl group of 1 to 4 carbon atoms, in particular methyl. For those compounds wherein one of the groups $R^2$ and $R^3$ represents alkyl, it is particularly preferred that the other of the groups $R^2$ and $R^3$ is hydrogen. Expecially preferred compounds are those wherein $R^1$ is methyl and $R^2$ and $R^3$ are hydrogen or methyl.

Example of preferred compounds according to formula (I) above are:

3-(3,4-epoxy-4-methylcyclohexyl)butanal
3-(4-hydroxy-4-methylcyclohexyl)butanal
3-(1,4-dimethyl-3,4-epoxycyclohexyl)propanal
3-(1,4-dimethyl-4-hydroxycyclohexyl)propanal.

The compounds of the invention may be prepared by a process which comprises hydroformylating an olefin of formula (II):

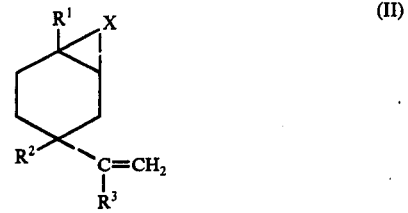

(II)

in the presence of a metal carbonyl catalyst. The catalyst may be a cobalt or rhodium carbonyl catalyst but is preferably a rhodium carbonyl complex, in particular a complex which also contains hydride and/or phosphine groups. The catalyst may be a homogeneous catalyst such as the compound $HRh(CO)(P(C_6H_5)_3)_3$ or a heterogeneous catalyst obtained, for example, by incorporating such a compound onto a solid carrier such as silica. The temperature of the hydroformylation is preferably from 50° 200° C. and the total pressure of the carbon monoxide and hydrogen used is preferably up to 200 atm. The process may be carried out in an organic solvent, for example, an aliphatic, cycloaliphatic or aromatic hydrocarbon.

The olefinic starting materials of formula (II) which are useful in preparing the compounds of the invention may be obtained from a variety of natural or synthetic sources. For example, crude turpineols obtained from commercial pine oils typically contain significant quantities of suitable alkenyl-hydroxy cyclohexane starting materials. Further, substituted vinylcyclohexenes obtained from synthetic sources such as isoprene dimerization can be epoxidized by known techniques - e.g., reaction with an organic hydroperoxide, such as tertiary butyl hydroperoxide over a titanium dioxide/silica catalyst - or hydroxylated for example, by reaction with formic acid and subsequent saponification, to provide the vinyl-epoxy-or hydroxy cyclohexane starting materials for the compounds of the invention.

As mentioned above, the compounds of the invention possess distinctive floral odors and therefore, are of interest as aroma chemicals in particular for use in perfumes and perfumed products such as soaps, deodorants, detergents and aerosols.

The invention is illustrated further in the following Examples. The NMR spectra were obtained at 60 MHz using solutions in deuterochloroform; the absorptions quoted are in ppm relative to a tetramethylsilane standard.

EXAMPLE I

The hydroformylation catalyst used was a heterogeneous catalyst formed by reacting silica with a preformed complex of of $(C_2H_5O)_3$-$SiCH_2CH_2$:$(C_6H_5)_2$ with $RhH(CO)[P(C_6H_5)_3]_3$.

Crude terpineol (20 g. containing 20–25% w 2-(4-hydroxy-4-methylcyclohexyl)propene), the hydroformylation catalyst (2.0 g), benzene (5 ml) and cyclohexane (20 ml) were mixed in a 100 ml stainless steel autoclave. The autoclave was then pressurized to 50–55 atm with a mixture of equal volumes of carbon monoxide and hydrogen. The autoclave contents were then stirred at 100° C. for 4.5 hours. After cooling to room temperature, the reaction mixture was filtered and distilled. The desired product 3-(4-hydroxy-4-methylcyclohexyl)butanal was obtained in a yield of 3.8 g, b.p. 106°–109° C. at 0.6 mm Hg. The NMR spectrum of the compound showed the following characteristic absorptions:

δ = 9.79 ppm (triplet, —CHO)
δ = 2.35 ppm (multiplet, —CH₂CHO)
δ = 1.20, 1.17 ppm (singlets, ring CH₃)
δ = 0.93 ppm (doublet, >CH—CH₃)

The compound possesses a mild floral odor reminiscent of lilac and Muguet.

EXAMPLE II

The starting material was limonene epoxide (2-(3,4-epoxy-4-methyl-cyclohexyl)propene (b.p. 76° C. at 13 mm Hg) which was prepared by epoxidizing limonene with t-butyl hydrogen peroxide in the presence of a titanium dioxide /silica catalyst.

Limonene epoxide (9.5 g), the hydroformylation catalyst of Example I (1.0 g), benzene (1.0 ml) and cyclohexane (10 ml) were mixed in a 100 ml stainless steel autoclave. The autoclave was then pressurized to 70 atm with a mixture of equal volumes of carbon monoxide and hydrogen. The reaction mixture was then stirred at 100° C. for 4 hours. The cooled reaction mixture was then distilled to give the desired 3-(3,4-epoxy-4-methyl cyclohexyl)butanal b.p. 91° C. at 13 mm Hg. The NMR spectrum of the compound showed the following characteristic absorptions:

δ = 9.81 ppm (triplet, —CHO)
δ = 2.88, 2.97 ppm (singlets, 1H)
δ = 1.28 ppm (singlet, ring CH₃)
δ = 0.88 ppm (doublet, >CH-CH₃)

The compound has a sweet green fruity floral odor.

EXAMPLE III (a) 1,4-Dimethyl-4-vinylcyclohex-1-ene (50 ml) and 98% w formic acid (100 ml) were stirred together for 18 hours at room temperature. The upper layer was then separated, diluted with cyclohexane and washed with water. The cyclohexane was then distilled off and the crude formate ester residue saponified with aqueous methanolic sodium hydroxide. The 1,4-dimethyl-4vinylcyclohexane-1-ol was recovered by distillation, b.p. 94°–97° C. at 20 mm Hg.

(b) 1,4-Dimethyl-4-vinylcyclohexan-1-ol (4.0 g) was hydroformylated at a pressure of 65 atm in a similar manner to that described in Example I and the desired 3-(1,4-dimethyl-4-hydroxycyclohexyl)propanal was recovered by distillation b.p. 130°–134° C. at 2 mm Hg. The NMR spectrum of the compound showed the following absorptions:

δ = 9.85 ppm (multiplet, -CHO)
δ = 2.40 ppm (triplet,

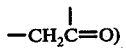
—CH₂C=O)

δ = 1.21 ppm (singlet, 4-CH₃)
δ = 0.89m 0.86 ppm (singlets, 1-CH₃)

The compound has a green piney/floral odor.

EXAMPLE IV

The starting material was 1,4-dimethyl-3,4-epoxy-4-vinylcyclohexane (b.p. 116°–120° C. at 130 mm Hg) which was prepared by epoxidizing 1,4-dimethyl-4-vinylcyclohex-1-ene with t-butyl hydrogen peroxide in the presence of a titanium dioxide /silica catalyst.

1,4-Dimethyl-3,4-epoxy-4-vinylcyclohexane (10.5 g) was hydroformylated at a pressure of 85-90 atm in a similar manner to that described in Example I and the desired 3-(1,4-dimethyl-3,4-epoxycyclohexyl) propanal was recovered by distillation, b.p. 119°–122° C. at 4 mm Hg. The NMR spectrum of the compound showed the following absorptions:

δ = 9.83, 9.78 ppm (triplets, CHO)
δ = 2.90 ppm (multiplet,

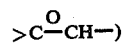
>C—CH—)

δ = 2.39 ppm (triplet,

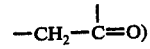
—CH₂—C=O)

δ = 1.32 ppm (singlet, 4-CH)
δ = 0.83, 0.81 ppm (singlet, 1-CH₃)

The compound possesses a sweet fruity melon-like odor.

What is claimed is:

1. Cyclohexane derivative to the formula:

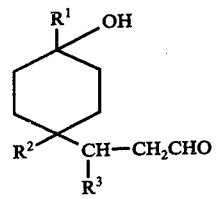

wherein R¹ represents an alkyl group, of 1 to 4 carbon atoms R² and R³ each represents a hydrogen atom or an alkyl group of 1 to 4 carbon atoms.

2. The cyclohexane derivative according to claim 1, in which R¹ is methyl and R² and R³ each represent hydrogen or methyl.

3. The cylohexane derivative according to claim 1 in which one of the groups R² and R³ is hydrogen when the other of the groups R² and R³ represents alkyl.

4. 3-(4-hydroxy-4-methylcyclohexyl)butanal.

5. 3-(1,4-dimethyl-4-hydroxycyclohexyl)propanal.

* * * * *